US012576261B2

(12) United States Patent
Vasudevan Jalaja et al.

(10) Patent No.: US 12,576,261 B2
(45) Date of Patent: Mar. 17, 2026

(54) ACCOUNT FOR PRELOAD CHANGES IN THE LEFT VENTRICLE

(71) Applicant: Boston Scientific Scimed, Inc., Maple Grove, MN (US)

(72) Inventors: Neethu Lekshmi Vasudevan Jalaja, Austin, TX (US); Carlos Reyes, Davie, FL (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 289 days.

(21) Appl. No.: 18/263,771

(22) PCT Filed: Feb. 1, 2022

(86) PCT No.: PCT/US2022/014645
§ 371 (c)(1),
(2) Date: Aug. 1, 2023

(87) PCT Pub. No.: WO2022/169720
PCT Pub. Date: Aug. 11, 2022

(65) Prior Publication Data
US 2024/0066281 A1 Feb. 29, 2024

Related U.S. Application Data

(60) Provisional application No. 63/144,582, filed on Feb. 2, 2021.

(51) Int. Cl.
*A61M 60/178* (2021.01)
*A61M 60/216* (2021.01)
(Continued)

(52) U.S. Cl.
CPC ........ *A61M 60/178* (2021.01); *A61M 60/216* (2021.01); *A61M 60/422* (2021.01); *A61M 60/538* (2021.01)

(58) Field of Classification Search
CPC ............ A61M 2205/18; A61M 60/178; A61M 60/216; A61M 60/232; A61M 60/422; A61M 60/538; A61M 60/546
See application file for complete search history.

(56) References Cited

U.S. PATENT DOCUMENTS

| | | | |
|---|---|---|---|
| 6,688,861 B2 | 2/2004 | Wampler |
| 7,575,423 B2 | 8/2009 | Wampler |

(Continued)

FOREIGN PATENT DOCUMENTS

| | | | |
|---|---|---|---|
| AU | 2006235839 A1 | 5/2007 |
| EP | 1402907 A1 | 3/2004 |

(Continued)

OTHER PUBLICATIONS

International Search Report and Written Opinion of International Application No. PCT/US2022/014645 dated May 12, 2022, 5 pp.

*Primary Examiner* — Scott Luan
(74) *Attorney, Agent, or Firm* — Seager Tufte & Wickhem, LLP

(57) ABSTRACT

A method of estimating a patient's cardiac preload in a patient having an implantable blood pump. The method includes generating a current waveform from operation of the implanted blood pump. A beat-to-beat pump filling index (PFI) is calculated, the PFI is calculated by dividing a current amplitude component by a time component, the amplitude component being calculated by subtracting a trough of the current waveform from an inflection point divided by an amplitude difference of peak to trough of the waveform, the time component being calculated by dividing a time between the trough and the inflection point by a time between the peak and the trough. An alert is generated if the PFI deviates from predetermined thresholds.

20 Claims, 6 Drawing Sheets

(51) Int. Cl.
    *A61M 60/422*        (2021.01)
    *A61M 60/538*        (2021.01)

(56)                References Cited

U.S. PATENT DOCUMENTS

| | | |
|---|---|---|
| 7,976,271 B2 | 7/2011 | LaRose et al. |
| 8,419,609 B2 | 4/2013 | Shambaugh, Jr. et al. |
| 10,159,775 B2 | 12/2018 | Voskoboynikov et al. |
| 10,376,162 B2 | 8/2019 | Edelman et al. |
| 10,688,232 B2 | 6/2020 | Voskoboynikov et al. |
| 11,707,617 B2 | 7/2023 | Reyes et al. |
| 2016/0166211 A1 | 6/2016 | Brown et al. |
| 2018/0311422 A1* | 11/2018 | Greatrex ............. A61M 60/824 |
| 2020/0060559 A1 | 2/2020 | Edelman et al. |

FOREIGN PATENT DOCUMENTS

| | | | |
|---|---|---|---|
| WO | 2006029216 A2 | 3/2006 | |
| WO | 2022169720 A1 | 8/2022 | |

* cited by examiner

ACCOUNT FOR PRELOAD CHANGES IN THE LEFT VENTRICLE

This application is a U.S. National Stage entry under 35 U.S.C. § 371 of International Application No. PCT/US2022/014645, filed Feb. 1, 2022, which claims priority from and the benefit of U.S. Provisional Patent Application No. 63/144,582, filed on Feb. 2, 2021, the entire content of each of which is incorporated herein by reference.

FIELD

The present application is generally related to implantable blood pumps, and in particular, a method of determining a patient with an implantable blood pump's cardiac preload.

BACKGROUND

Implantable blood pumps may be used to provide assistance to patients with late-stage heart disease. Blood pumps operate by receiving blood from a patient's vascular system and impelling the blood back into the patient's vascular system. By adding momentum and pressure to the patient's blood flow, blood pumps may augment or replace the pumping action of the heart. For example, a blood pump may be configured as a ventricular assist device or "VAD." Where a VAD is used to assist the pumping action of the left ventricle, the device draws blood from the left ventricle of the heart and discharges the blood into the aorta.

In cardiac physiology preload is defined as the initial stretching of the cardiac myocytes prior to contraction. The sarcomere length cannot be determined directly, other indices of preload such as left atrial pressure (LAP), left ventricular end diastolic pressure, and ventricular end diastolic volume (EDV) are used to define the preload. In a failing heart, preload will not necessarily increase the stroke volume as the ventricle cannot be stretched more which can lead to systemic congestion or edema. In mechanical circulatory support (MCS) therapy, the VAD is placed in the left and/or right ventricle to assist the failing ventricle to migrate the available/residual volume of blood from ventricle into the systemic/pulmonary circulation for appropriate perfusion. Operating the pump at a predetermined set speed maintains the physiologically suitable output and prevent ventricle overfilling/suction which arises due to under/over pumping. However, current VAD devices do not have an efficient preload tracking method to derive the preload information.

SUMMARY

The techniques of this disclosure generally relate to implantable blood pumps, and in particular, a method of determining a patient with an implantable blood pump's cardiac preload.

In one aspect, the present disclosure provides a method of estimating a patient's cardiac preload in a patient having an implantable blood pump. The method includes generating a current waveform from operation of the implanted blood pump. A beat-to-beat pump filling index (PFI) is calculated, the PFI is calculated by dividing a current amplitude component by a time component, the amplitude component being calculated by subtracting a trough of the current waveform from an inflection point divided by the amplitude difference of peak to trough of the waveform, the time component being calculated by dividing a time between the trough and the inflection point by a time between the peak and the trough. An alert is generated if the PFI deviates from predetermined thresholds.

In another aspect of this embodiment, the predetermined thresholds include an upper threshold and a lower threshold different than the upper threshold.

In another aspect of this embodiment, the alert is generated if a median PFI calculated from a prior 5 consecutive beat-to-beat calculations of the PFI is greater than the upper threshold or lower than the lower threshold.

In another aspect of this embodiment, the method further includes increasing a speed of an impeller of the implantable blood if the median PFI exceeds the upper threshold.

In another aspect of this embodiment, the method further includes decreasing a speed of an impeller of the implantable blood if the median PFI drops below the lower threshold.

In another aspect of this embodiment, the upper threshold is determined by multiplying a twentieth percentile of the PFI from a prior 10 consecutive beat-to-beat calculations of PFI by 1.2, and the lower threshold is determined by multiplying an eightieth percentile of the PFI from the prior 10 consecutive beat-to-beat calculations of PFI by 0.8.

In another aspect of this embodiment, the alert is recorded and displayed in a log-file.

In another aspect of this embodiment, the method further includes increasing or decreasing a speed of an impeller of the implantable blood pump based on the alert.

In another aspect of this embodiment, the increasing or decreasing of the speed of the impeller of the implantable blood pump is either automatic or clinician initiated.

In another aspect of this embodiment, the alert is indicative of either a high cardiac preload or a low cardiac preload.

In one aspect, a controller for an implantable blood pump includes processing circuitry configured to generate a current waveform from operation of the implanted blood pump. A beat-to-beat pump filling index (PFI) is calculated, the PFI being calculated by dividing a current amplitude component by a time component, the amplitude component being calculated by subtracting a trough of the current waveform from an inflection point divided by the amplitude difference of peak to trough of the waveform, the time component being calculated by dividing a time between the trough and the inflection point by a time between the peak and the trough. An alert is generated if the PFI deviates from predetermined thresholds.

In another aspect of this embodiment, the predetermined thresholds include an upper threshold and a lower threshold different than the upper threshold.

In another aspect of this embodiment, the alert is generated if a median PFI calculated from a prior 5 consecutive beat-to-beat calculations of the PFI is greater than the upper threshold or lower than the lower threshold.

In another aspect of this embodiment, the processing circuitry is further configured to increase a speed of an impeller of the implantable blood if the median PFI exceeds the upper threshold.

In another aspect of this embodiment, the processing circuitry is further configured to decrease a speed of an impeller of the implantable blood if the median PFI drops below the lower threshold.

In another aspect of this embodiment, the upper threshold is determined by multiplying a twentieth percentile of the PFI from a prior 10 consecutive beat-to-beat calculations of PFI by 1.2, and the lower threshold is determined by multiplying an eightieth percentile of the PFI from the prior 10 consecutive beat-to-beat calculations of PFI by 0.8.

In another aspect of this embodiment, the processing circuitry is further configured to record and display the alert in a log-file.

In another aspect of this embodiment, the processing circuitry is further configured to increase or decrease a speed of an impeller of the implantable blood pump based on the alert.

In another aspect of this embodiment, the alert is indicative of either a high cardiac preload or a low cardiac preload.

In one aspect, a controller for an implantable blood pump includes processing circuitry configured to generate a current waveform from operation of the implanted blood pump. A beat-to-beat pump filling index (PFI) is calculated, the PFI being calculated by dividing a current amplitude component by a time component, the amplitude component being calculated by subtracting a trough of the current waveform from an inflection point divided by the amplitude difference of peak to trough of the waveform, the time component being calculated by dividing a time between the trough and the inflection point by a time between the peak and the trough. A set speed of an impeller of the implantable blood pump is increased or decreased if the PFI deviates from predetermined thresholds.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Figure 1:
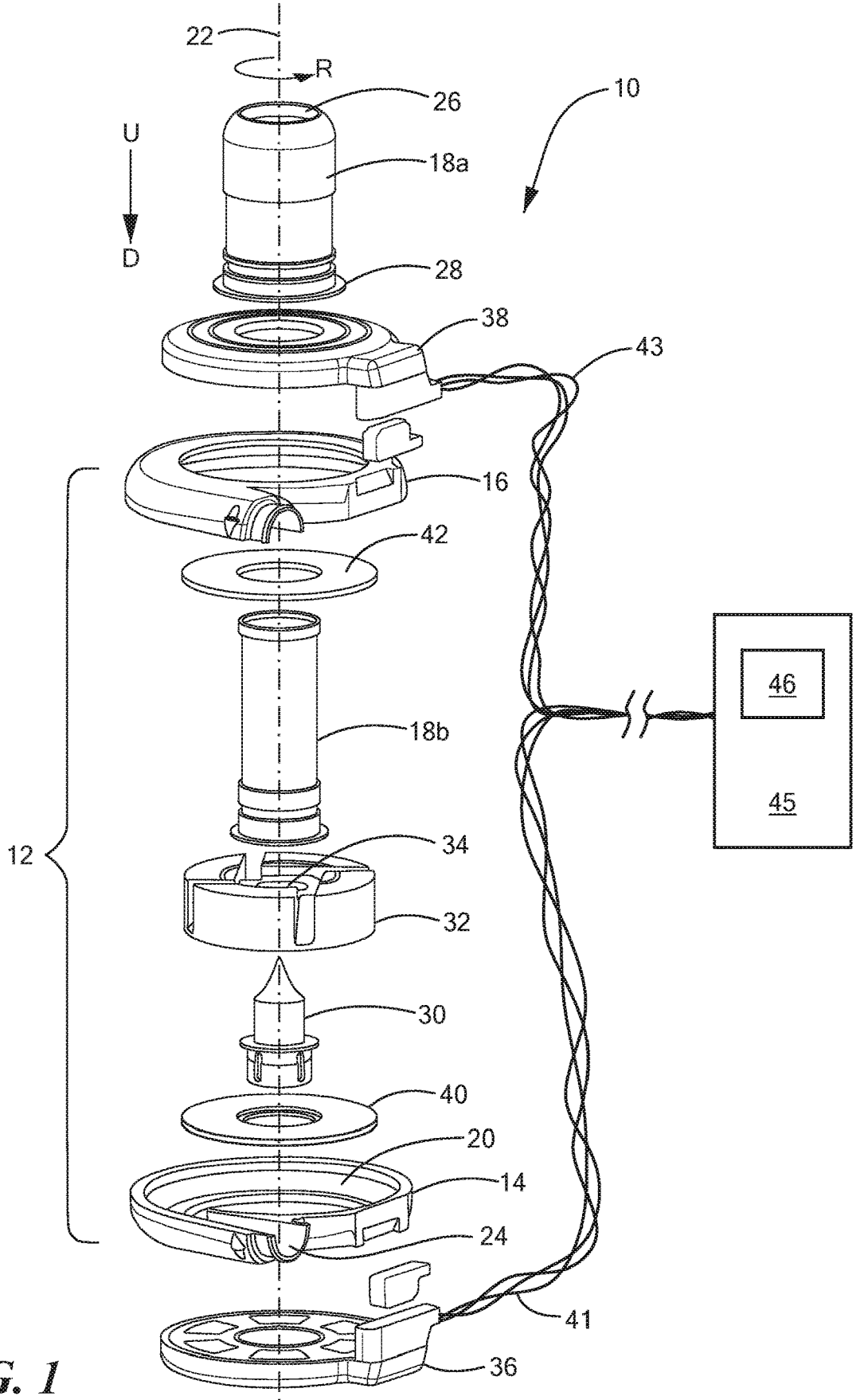
FIG. 1 is a disassembled view of an implantable blood pump constructed in accordance with the principles of the present application.

Referring now to the drawings in which like reference designators refer to like elements there is shown in FIG. 1 an exemplary sensorless blood pump constructed in accordance with the principles of the present application and designated generally "10." The blood pump 10 according to one embodiment of the disclosure includes a static structure or housing 12 which houses the components of the blood pump 10. In one configuration, the housing 12 includes a lower housing or first portion 14, an upper housing or second portion 16, and an inlet portion or inflow cannula 18 which includes an outer tube 18a and an inner tube 18b. The first portion 14 and the second portion 16 cooperatively define a volute shaped chamber 20 having a major longitudinal axis 22 extending through the first portion and inflow cannula 18. The chamber 20 defines a radius that increases progressively around the axis 22 to an outlet location on the periphery of the chamber 20. The first portion 14 and the second portion 16 define an outlet 24 in communication with chamber 20. The first portion 14 and the second portion 16 also define isolated chambers (not shown) separated from the volute chamber 20 by magnetically permeable walls.

The inflow cannula 18 is generally cylindrical and extends from first portion 14 and extends generally along axis 22. The inflow cannula 18 has an upstream end or proximal end 26 remote from second portion 16 and a downstream end or distal end 28 proximate the chamber 20. The parts of the housing 12 mentioned above are fixedly connected to one another so that the housing 12 as a whole defines a continuous enclosed flow path. The flow path extends from upstream end 26 at the upstream end of the flow path to the outlet 24 at the downstream end of the flow path. The upstream and downstream directions along the flow path are indicated in FIG. 1 by the arrows U and D respectively. A post 30 is mounted to first portion 14 along axis 22. A generally disc shaped ferromagnetic rotor 32 with a central hole 34 is mounted within chamber 20 for rotation about the axis 22. Rotor 32 includes a permanent magnet and also includes flow channels for transferring blood from adjacent the center of the rotor 32 to the periphery of the rotor 32. In the assembled condition, post 30 is received in the central hole of the rotor 32. A first stator 36 having a plurality of coils may be disposed within the first portion 14 downstream from the rotor 32. The first stator 36 may be axially aligned with the rotor along axis 22 such that when a current is applied to the plurality of coils in the first stator 36, the electromagnetic forces generated by the first stator 36 rotate the rotor 32 and pump blood. A second stator 38 may be disposed within the second portion 16 upstream from the rotor 32. The second stator 38 may be configured to operate in conjunction with or independently of the first stator 36 to rotate the rotor 32.

Electrical connectors 41 and 43 are provided on the first stator 36 and the second stator 38 respectively for connecting the coils to a source of power such as a controller 45, which may be implanted or external to the patient. The controller 45 having processing circuitry 46 is configured to apply power to the coils of the pump to create a rotating magnetic field which spins rotor 32 around axis 22 in a predetermined first direction of rotation, such as the direction R indicated by the arrow in FIG. 1, i.e., counterclockwise as seen from the upstream end of inflow cannula 18. In other configurations of the blood pump 10, the first direction may be clockwise. Rotation of the rotor 32 impel blood downstream along the flow path so that the blood, moves in a downstream direction D along the flow path, and exits through the outlet 24. During rotation, hydrodynamic and magnetic bearings (not shown) support the rotor 32 and maintain the rotor 32 out of contact with elements of the first portion 14 and the second portion 16 during operation, as discussed in more detail below. The general arrangement of the components described above may be similar to the blood pump 10 used in the MCSD sold under the designation HVAD by HeartWare, Inc., assignee of the present application. The arrangement of components such as the magnets, electromagnetic coils, and hydrodynamic bearings used in such a pump and variants of the same general design are described in U.S. Pat. Nos. 6,688,861; 7,575,423; 7,976, 271; and 8,419,609, the disclosures of which are hereby incorporated by reference herein.

Figure 2:
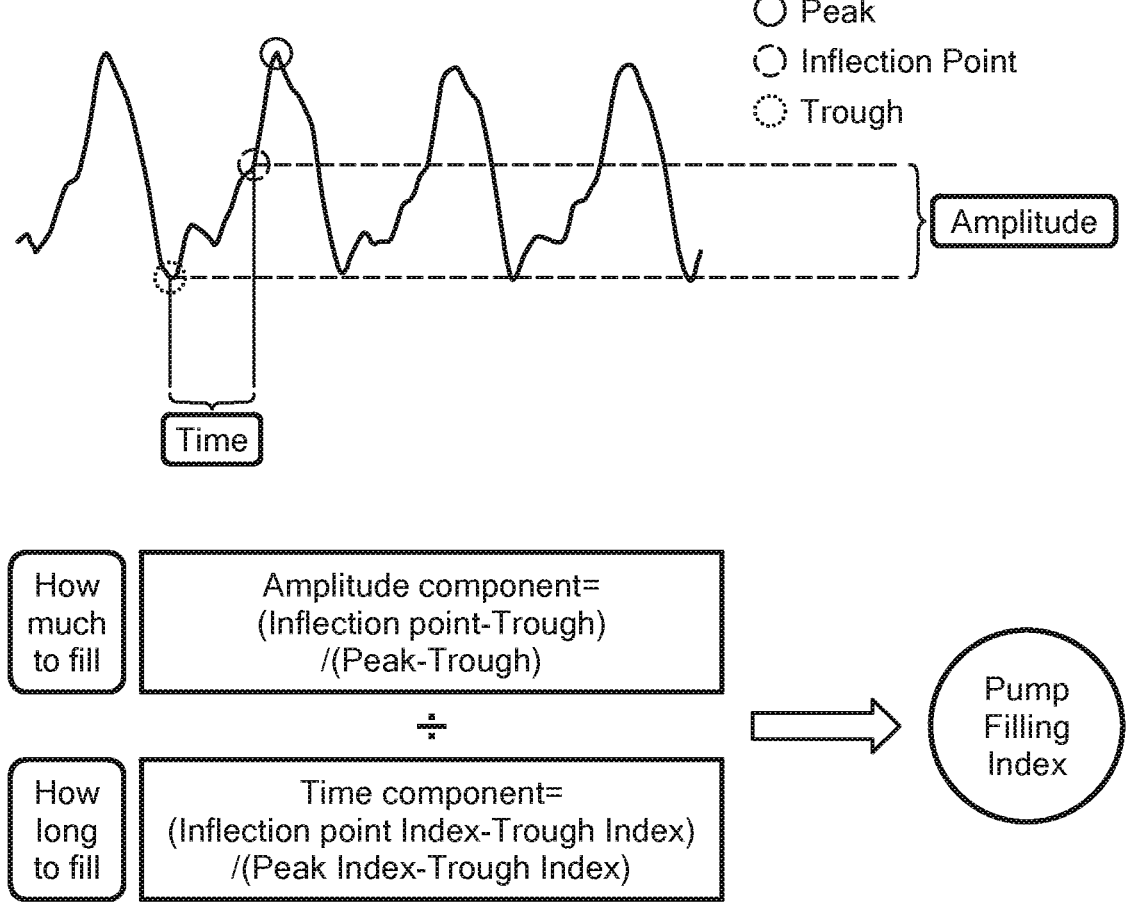
FIG. 2 shows an exemplary beat-by-beat cardiac waveform and an equation for calculation a pump filling index (PFI)
Figure 3:
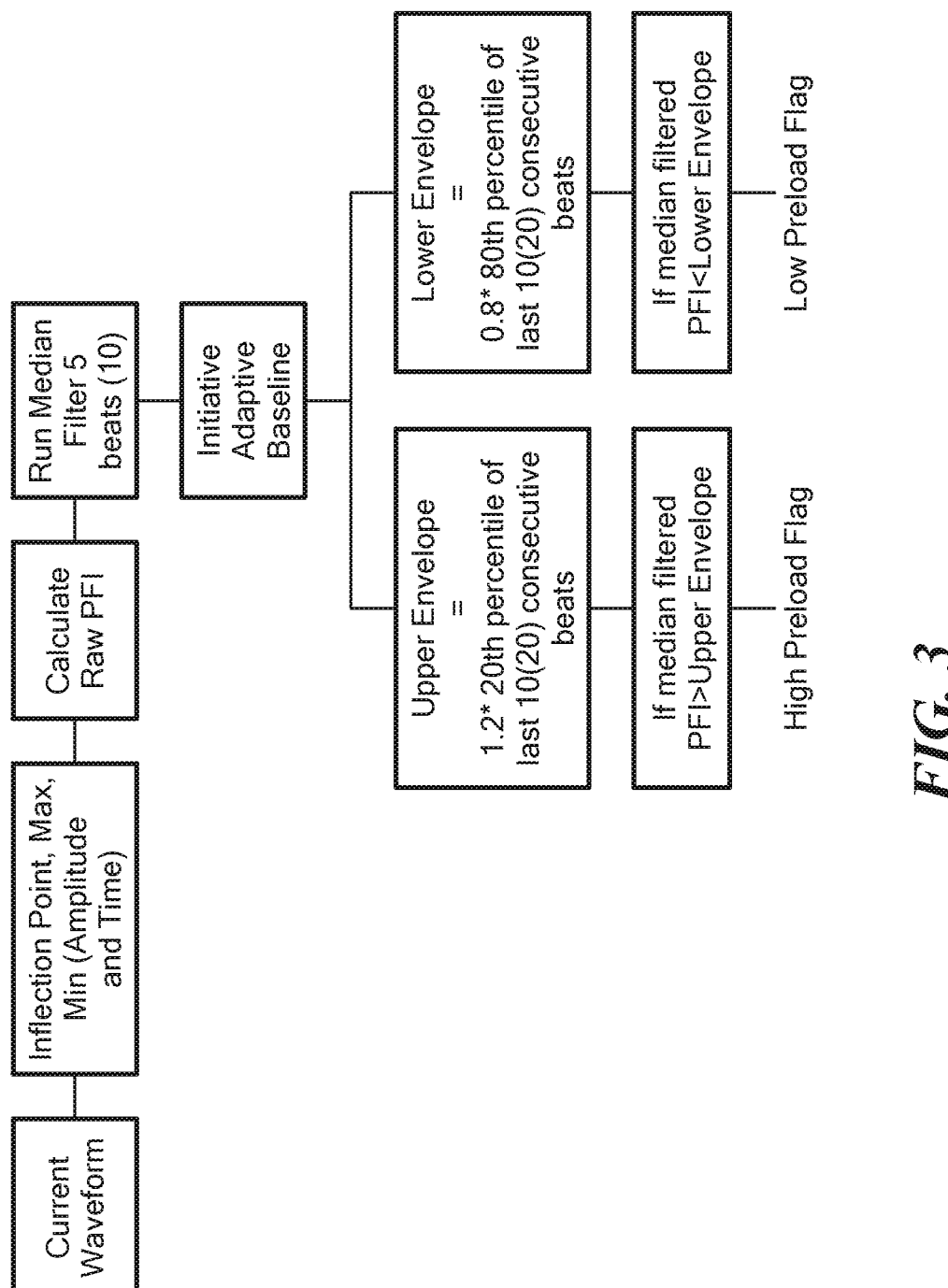
FIG. 3 is a flow chart showing an exemplary method estimating a patient's cardiac preload.
Figure 4:
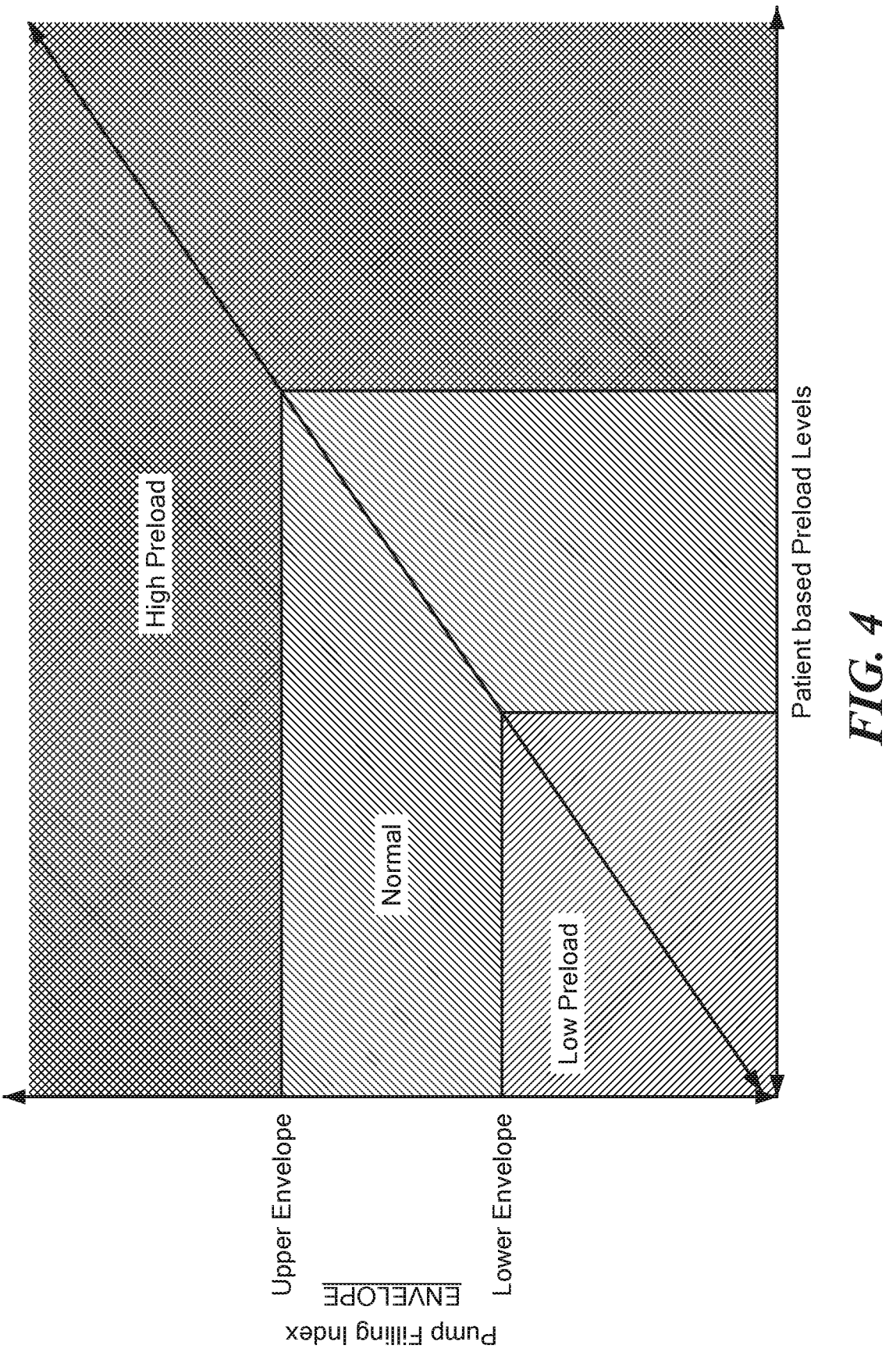
FIG. 4 is a graph showing a linear relationship between PFI and a patient's cardiac preload.
Figure 5:
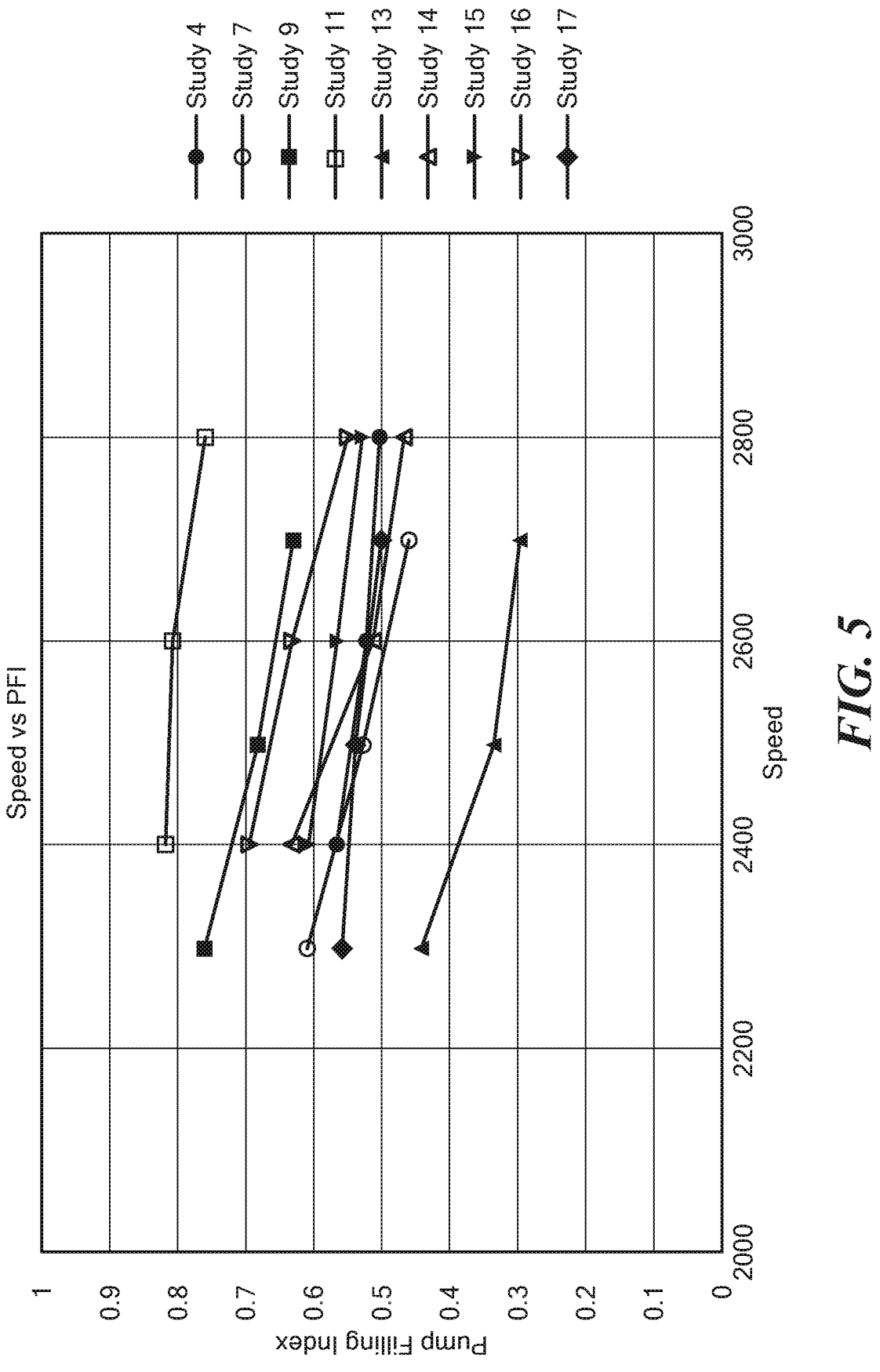
FIG. 5 is a graph showing a relationship between PFI and pump speed.
Figure 6:
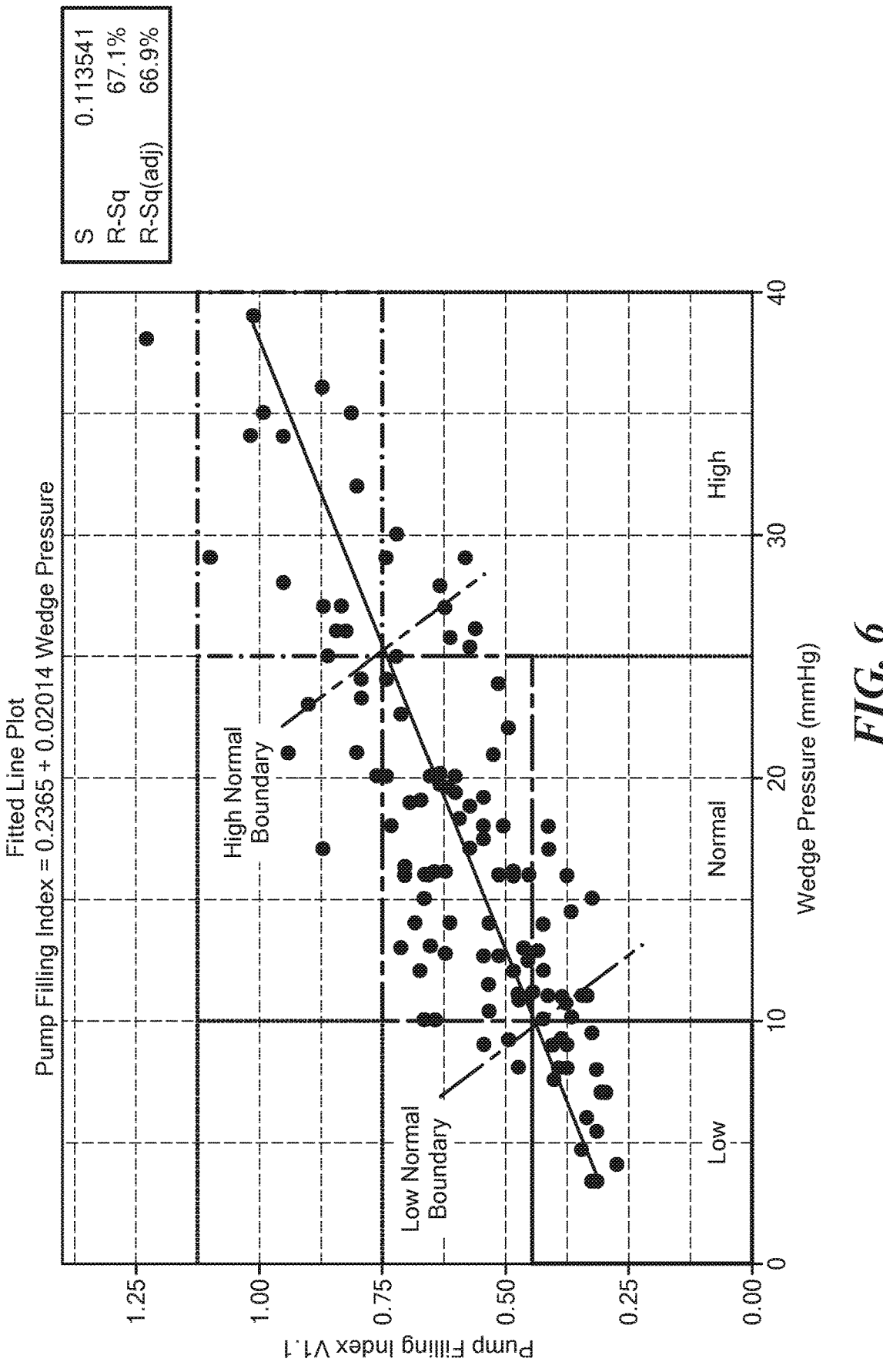
FIG. 6 is a graph showing a linear relationship with wedge pressure and PFI.

Referring now to FIGS. 2-6, the processing circuitry 46 is configured to generate a current or flow waveform during operation of the implantable blood pump 10 (Step 102). For example, as shown in FIG. 2, the current waveform includes cardiac beat-to-beat peaks and troughs which correspond to the beating heart as blood is pumped. Between each peak and trough is an inflection point at which the waveform changes from positive to negative current. The method of determining the location of the inflection point is disclosed in U.S. patent application Ser. No. 17/095,096, the entirety of which is expressly incorporate by reference herein. For each cardiac beat, a pump filling index (PFI) which is a relative index of cardiac preload is calculated (Step 104). In particular, the PFI may be calculated by dividing a current amplitude component by a time component, the amplitude component being calculated by subtracting a trough of the current waveform from an inflection point divided by the amplitude difference of peak to trough of the waveform, the time component being calculated by dividing a time between the trough and the inflection point by a time between the peak and the trough. In general, a lower PFI number is indicative of a lower cardiac preload, whereas a higher PFI is indicative of a higher cardiac preload. However, the raw PFI data is filtered to determine what action, if any, should be taken by the clinician or automatically by the controller. In particular, a median PFI is calculated based on a prior number of cardiac beats, for example, the previous 5 beats following an initial 10 beats Step (106). The median PFI data may be recorded and displayed in a log file of the controller 15. An upper threshold and a lower threshold are calculated. In one configuration the upper threshold is calculated by multiplying the $20^{th}$ percentile of the last 10 beats, following an initial 20 beats, by 1.2 (Step 108) and the lower threshold is calculated by multiplying the $80^{th}$ percentile of the last 10 beats, following an initial 20 beats, by 0.8 (Step 110). These percentiles and the constant multiplier are exemplary and other constants and percentiles are contemplated by this invention. An alert is generated, either in real-time or in the log file of the controller 45, if the PFI deviates from predetermined thresholds (Step 112). As shown in FIG. 4, the PFI has linear relationship with cardiac preload levels, such that an upper envelope and lower envelope for cardiac preload are formed. Moreover, a clinician may use the alerts generated by the controller 45 is a decision point on whether to change a preset speed of the impeller 32 of the pump 10 in an open loop system, or optionally, the controller 45 may automatically change the speed of the impeller 32 of the pump as a function of the PFI alert in a closed loop system. For example, as shown in FIG. 5, as the speed of the impeller 32 is increased the PFI decreases and when the speed of the impeller 32 is decreased, the PFI increases. Thus, speed changes are correlated to cardiac preload such that the clinician or controller can modulate the speed of the impeller 32 based on the PFI. As shown in FIG. 6, the calculated PFI also has a linear correlation with pulmonary capillary wedge pressure (PCWP) which is the traditional and invasive method of measuring left ventricular pressure. Thus, the PFI may be a substitute for estimating cardiac preload.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

Example 1: A method of estimating a patient's cardiac preload in a patient having an implantable blood pump, the method comprising:

generating a current waveform from operation of the implanted blood pump;

calculating a beat-to-beat pump filling index (PFI), the PFI being calculated by dividing a current amplitude component by a time component, the amplitude component being calculated by subtracting a trough of the current waveform from an inflection point divided by an amplitude difference of peak to trough of the waveform, the time component being calculated by dividing a time between the trough and the inflection point by a time between the peak and the trough; and generating an alert if the PFI deviates from predetermined thresholds.

Example 2: The method of Example 1, wherein the predetermined thresholds include an upper threshold and a lower threshold different than the upper threshold.

Example 3: The method of Example 2, wherein the alert is generated if a median PFI calculated from a prior 5 consecutive beat-to-beat calculations of the PFI is greater than the upper threshold or lower than the lower threshold.

Example 4: The method of Example 3, further including increasing a speed of an impeller of the implantable blood if the median PFI exceeds the upper threshold.

Example 5: The method of Example 3, further including decreasing a speed of an impeller of the implantable blood if the median PFI drops below the lower threshold.

Example 6: The method of Example 3, wherein the upper threshold is determined by: multiplying a twentieth percentile of the PFI from a prior 10 consecutive beat-to-beat calculations of PFI by 1.2; and wherein the lower threshold is determined by:

multiplying an eightieth percentile of the PFI from the prior 10 consecutive beat-to-beat calculations of PFI by 0.8.

Example 7: The method of Example 1, wherein the alert is recorded and displayed in a log-file.

Example 8: The method of Example 7, further including increasing or decreasing a speed of an impeller of the implantable blood pump based on the alert.

Example 9: The method of Example 8, wherein the increasing or decreasing of the speed of the impeller of the implantable blood pump is either automatic or clinician initiated.

Example 10: The method of Example 1, wherein the alert is indicative of either a high cardiac preload or a low cardiac preload.

Example 11: A controller for an implantable blood pump, comprising:

processing circuitry configured to:

generate a current waveform from operation of the implanted blood pump;

calculate a beat-to-beat pump filling index (PFI), the PFI being calculated by dividing a current amplitude component by a time component, the amplitude component being calculated by subtracting a trough of the current waveform from an inflection point divided by an amplitude difference of peak to trough of the waveform, the time component being calculated by dividing a time between the trough and the inflection point by a time between the peak and the trough; and generate an alert if the PFI deviates from predetermined thresholds.

Example 12: The controller of Example 11, wherein the predetermined thresholds include an upper threshold and a lower threshold different than the upper threshold.

Example 13: The controller of Example 12, wherein the alert is generated if a median PFI calculated from a prior 5 consecutive beat-to-beat calculations of the PFI is greater than the upper threshold or lower than the lower threshold.

Example 14: The controller of Example 13, wherein the processing circuitry is further configured to increase a speed of an impeller of the implantable blood if the median PFI exceeds the upper threshold.

Example 15: The controller of Example 13, wherein the processing circuitry is further configured to decrease a speed of an impeller of the implantable blood if the median PFI drops below the lower threshold.

Example 16: The controller of Example 13, wherein the upper threshold is determined by:

multiplying a twentieth percentile of the PFI from a prior 10 consecutive beat-to-beat calculations of PFI by 1.2; and wherein the lower threshold is determined by:

multiplying an eightieth percentile of the PFI from the prior 10 consecutive beat-to-beat calculations of PFI by 0.8.

Example 17: The controller of Example 11, wherein the processing circuitry is further configured to record and display the alert in a log-file.

Example 18: The controller of Example 17, wherein the processing circuitry is further configured to increase or decrease a speed of an impeller of the implantable blood pump based on the alert.

Example 19: The controller of Example 11, wherein the alert is indicative of either a high cardiac preload or a low cardiac preload.

Example 20: A controller for an implantable blood pump, comprising:

processing circuitry configured to:

generate a current waveform from operation of the implanted blood pump;

calculate a beat-to-beat pump filling index (PFI), the PFI being calculated by dividing a current amplitude component by a time component, the amplitude component being calculated by subtracting a trough of the current waveform from an inflection point divided by an amplitude difference of peak to trough of the waveform, the time component being calculated by dividing a time between the trough and the inflection point by a time between the peak and the trough; and increase or decrease a set speed of an impeller of the implantable blood pump if the PFI deviates from predetermined thresholds.

Various examples have been described. These and other examples are within the scope of the following claims.

What is claimed is:

1. A method of estimating a patient's cardiac preload in a patient having a blood pump, the method comprising:

generating a current waveform from operation of the blood pump;

calculating a beat-to-beat pump filling index (PFI), the PFI being calculated by dividing a current amplitude component by a time component, the amplitude component being calculated by subtracting a trough of the current waveform from an inflection point divided by an amplitude difference of peak to trough of the current waveform, the time component being calculated by dividing a time between the trough and the inflection point by a time between the peak and the trough; and generating an alert if the PFI deviates from predetermined thresholds.

2. The method of claim 1, wherein the predetermined thresholds include an upper threshold and a lower threshold different than the upper threshold.

3. The method of claim 2, wherein generating the alert comprises generating the alert in response to determining a median PFI calculated from a prior 5 consecutive beat-to-beat calculations of the PFI is greater than the upper threshold or lower than the lower threshold.

4. The method of claim 3, further including increasing a speed of an impeller of the blood pump if the median PFI exceeds the upper threshold.

5. The method of claim 3, further including decreasing a speed of an impeller of the blood pump if the median PFI drops below the lower threshold.

6. The method of claim 3, wherein the upper threshold is determined by:

multiplying a twentieth percentile of the PFI from a prior 10 consecutive beat-to-beat calculations of PFI by 1.2; and wherein the lower threshold is determined by:

multiplying an eightieth percentile of the PFI from the prior 10 consecutive beat-to-beat calculations of PFI by 0.8.

7. The method of claim 1, further comprising recording and displaying the alert in a log-file.

8. The method of claim 1, further including increasing or decreasing a speed of an impeller of the blood pump based on the alert.

9

9. The method of claim 8, wherein the increasing or decreasing of the speed of the impeller of the blood pump is either automatic or clinician initiated.

10. The method of claim 1, wherein the alert is indicative of either a high cardiac preload or a low cardiac preload.

11. A controller for a blood pump, the controller comprising:

processing circuitry configured to:

generate a current waveform from operation of the blood pump; calculate a beat-to-beat pump filling index (PFI), the PFI being calculated by dividing a current amplitude component by a time component, the amplitude component being calculated by subtracting a trough of the current waveform from an inflection point divided by an amplitude difference of peak to trough of the current waveform, the time component being calculated by dividing a time between the trough and the inflection point by a time between the peak and the trough; and generate an alert if the PFI deviates from predetermined thresholds.

12. The controller of claim 11, wherein the predetermined thresholds include an upper threshold and a lower threshold different than the upper threshold.

13. The controller of claim 12, wherein the processing circuitry is configured to generate the alert in response to determining a median PFI calculated from a prior 5 consecutive beat-to-beat calculations of the PFI is greater than the upper threshold or lower than the lower threshold.

14. The controller of claim 13, wherein the processing circuitry is further configured to increase a speed of an impeller of the blood pump if the median PFI exceeds the upper threshold.

15. The controller of claim 13, wherein the processing circuitry is further configured to decrease a speed of an impeller of the blood pump if the median PFI drops below the lower threshold.

16. The controller of claim 12, wherein the processing circuitry is configured to determine the upper threshold by at least multiplying a twentieth percentile of the PFI from a prior 10 consecutive beat-to-beat calculations of PFI by 1.2, and wherein the processing circuitry is configured to determine the lower threshold by at least multiplying an eightieth percentile of the PFI from the prior 10 consecutive beat-to-beat calculations of PFI by 0.8.

17. The controller of claim 11, wherein the processing circuitry is configured to increase or decrease a speed of an impeller of the blood pump based on the alert.

18. A controller for a blood pump, the controller comprising:

processing circuitry configured to:

generate a current waveform from operation of the blood pump;

calculate a beat-to-beat pump filling index (PFI), the PFI being calculated by dividing a current amplitude component by a time component, the amplitude component being calculated by subtracting a trough of the current waveform from an inflection point divided by an amplitude difference of peak to trough of the current waveform, the time component being calculated by dividing a time between the trough and the inflection point by a time between the peak and the trough; and increase or decrease a set speed of an impeller of the blood pump if the PFI deviates from a predetermined threshold.

19. The controller of claim 18, wherein the processing circuitry is configured to increase or decrease the set speed of the impeller by at least increasing the speed of the impeller if the PFI exceeds the predetermined threshold.

20. The controller of claim 18, wherein the processing circuitry is configured to increase or decrease the set speed of the impeller by at least decreasing the speed of the impeller if the PFI is less than the predetermined threshold.

* * * * *